US012285468B2

United States Patent
Jarstad et al.

(10) Patent No.: US 12,285,468 B2
(45) Date of Patent: Apr. 29, 2025

(54) LIQUID NEUROTOXIN FORMULATION STABILIZED WITH TRYPTOPHAN OR TYROSINE

(71) Applicant: IPSEN BIOPHARM LIMITED, Wrexham (GB)

(72) Inventors: Anders Jarstad, Uppsala (SE); Anna Friis, Uppsala (SE); Ulf Stahl, Uppsala (SE); Ann Gurell, Stockholm (SE); Barbro Agren, Mattmar (SE); Emilia Edstrom, Uppsala (SE); Andrew Pickett, Uppsala (SE)

(73) Assignee: IPSEN BIOPHARM LIMITED, Wrexham (GB)

(*) Notice: Subject to any disclaimer, the term of this patent is extended or adjusted under 35 U.S.C. 154(b) by 0 days.

(21) Appl. No.: 18/476,731

(22) Filed: Sep. 28, 2023

(65) Prior Publication Data

US 2024/0050539 A1  Feb. 15, 2024

Related U.S. Application Data

(63) Continuation of application No. 18/173,991, filed on Feb. 24, 2023, now abandoned, which is a continuation of application No. 17/304,888, filed on Jun. 28, 2021, now abandoned, which is a continuation of application No. 16/304,986, filed as application No. PCT/EP2017/062785 on May 26, 2017, now abandoned.

(30) Foreign Application Priority Data

May 27, 2016  (WO) ................. PCT/EP2016/062085

(51) Int. Cl.
| | |
|---|---|
| A61K 38/46 | (2006.01) |
| A61K 8/00 | (2006.01) |
| A61K 8/19 | (2006.01) |
| A61K 8/39 | (2006.01) |
| A61K 8/49 | (2006.01) |
| A61K 8/66 | (2006.01) |
| A61K 9/00 | (2006.01) |
| A61K 38/48 | (2006.01) |
| A61K 47/02 | (2006.01) |
| A61K 47/18 | (2017.01) |
| A61K 47/26 | (2006.01) |
| A61Q 19/08 | (2006.01) |

(52) U.S. Cl.
CPC ............ *A61K 38/4893* (2013.01); *A61K 8/00* (2013.01); *A61K 8/19* (2013.01); *A61K 8/39* (2013.01); *A61K 8/492* (2013.01); *A61K 8/66* (2013.01); *A61K 9/0019* (2013.01); *A61K 47/02* (2013.01); *A61K 47/183* (2013.01); *A61K 47/26* (2013.01); *A61Q 19/08* (2013.01)

(58) Field of Classification Search
CPC ... A61K 38/4893; A61K 47/183; A61K 47/26
See application file for complete search history.

(56) References Cited

U.S. PATENT DOCUMENTS

| | | | |
|---|---|---|---|
| 7,163,671 B2 | 1/2007 | Sato et al. | |
| 7,211,261 B1 | 5/2007 | Moyer et al. | |
| 7,829,525 B2 | 11/2010 | Frevert | |
| 7,879,341 B2 | 2/2011 | Taylor | |
| 8,617,568 B2 | 12/2013 | Jung et al. | |
| 9,107,815 B2 | 8/2015 | Hunt | |
| 2002/0064536 A1 | 5/2002 | Hunt | |
| 2003/0092622 A1 | 5/2003 | Sato et al. | |
| 2003/0118598 A1* | 6/2003 | Hunt ................. | A61K 38/4893 424/184.1 |
| 2006/0269575 A1 | 11/2006 | Hunt | |
| 2014/0161783 A1 | 6/2014 | Jung et al. | |

FOREIGN PATENT DOCUMENTS

| | | |
|---|---|---|
| EP | 0909564 B1 | 4/1999 |
| EP | 2170400 B1 | 7/2012 |
| EP | 2480250 B1 | 4/2014 |
| WO | 0158472 A2 | 8/2001 |
| WO | 2005007185 A2 | 1/2005 |
| WO | 2006005910 A2 | 1/2006 |
| WO | 2006013370 A1 | 2/2006 |
| WO | 2007144493 A2 | 12/2007 |

(Continued)

OTHER PUBLICATIONS

Rinalducci et al., Journal of Experimental Botany, 59:3781-3801 (2008).
International Search report issued for International Patent Application No. PCT/EP2017/062785, dated Aug. 21, 2017.
Written Opinion issued for International Patent Application No. PCT/EP2017/062785, dated Aug. 21, 2017.
Pickett, A., "Botulinum Toxin as a Clinical Product: Manufacture and Pharmacology," Chapter 2, Clinical Applications of Botulinum Neurotoxin, Springer Science+Business Media New York, 2014, pp. 7-49.
Shone, C.C. et al., "Growth of Clostridia and Preparation of Their Neurotoxins," Current Topics in Microbiology and mmunology, 195, 1995, pp. 151-154.

(Continued)

*Primary Examiner* — Mary Maille Lyons
(74) *Attorney, Agent, or Firm* — Sunit Talapatra; Foley & Lardner LLP

(57) ABSTRACT

The invention relates to stable liquid neurotoxin formulations which are free of animal proteins, comprising a surfactant, an amino acid selected from tryptophan and tyrosine, a buffer comprising sodium, chloride and phosphate ions, which have a pH between 5.5 and 8, and which are stable for 2 months. These compositions are suitable for use in therapy and in particular for administration to a patient to achieve a desired therapeutic or aesthetic effect. The invention also relates to the use of an amino acid selected from tryptophan and tyrosine to protect a proteinaceous neurotoxin from degradation in a liquid composition which is free of animal derived proteins.

16 Claims, No Drawings

Specification includes a Sequence Listing.

(56) References Cited

FOREIGN PATENT DOCUMENTS

| WO | 2009008595 A1 | 1/2009 |
| WO | 2012166943 A1 | 12/2012 |
| WO | 2013049508 A1 | 4/2013 |
| WO | 2015044416 A1 | 4/2015 |
| WO | 2015166242 A1 | 11/2015 |

OTHER PUBLICATIONS

Straughn, D., "Progress in Applying the Three Rs to the Potency Testing of Botulinum Toxin Type A," ATLA 34(3), 2006, pp. 305-313.

Hambleton, P. and A.M. Picket, "Potency equivalence of botulinum toxin preparations," Journal of the Royal Society of Medicine, 87.11, 1994, p. 719.
Hambleton, P. et al., "Production, purification and toxoiding of Clostridium botulinum type A toxin," Biomedical Aspects of Botulism, Eds_ G_ E. Lewis, Jr_ and P. s_ Angel, Academic Press, Inc., New York, USA, 1981, p. 248.
Bigalke, H. et al., "Botulinum Neurotoxins: Qualitative and Quantitative Analysis Using the Mouse Phrenic Nerve Hemidiaphragm Assay (MPN)," Toxins, 7.12, 2015, pp. 4895-4905.
Office Action in Eurasian Application No. 201892493, issued Nov. 29, 2019.
Office Action in Eurasian Application No. 201892493, issued May 20, 2020.
Office Action in corresponding Georgian Application No. AP 2017 14939, issued Apr. 11, 2019.
Office Action in corresponding Japanese Application No. 2018-562171, issued March 2, 2019
Office Action in corresponding Japanese Application No. 2018-562171, issued Oct. 12, 2019.
Office Action in corresponding South Korean Application No. 10-2018-7037095, issued Jul. 28, 2021.
First Office Action in corresponding Macanese Application No. I/001613.
First Office Action in corresponding Russian Application No. 2018142149/04.
First Office Action in corresponding Saudi Application No. 206/13359.
Office Action in corresponding Singaporean Application No. 11201810561Y, issued Apr. 3, 2020.
Office Action in corresponding Taiwanese Application No. 106117499, issued Jun. 10, 2021.
Office Action in corresponding Uzbek Application No. IAP 20180568/4, issued Apr. 15, 2021.
Office Action in corresponding Israeli Application No. 263173 (Abstract).
First Office Action in corresponding Thai Application No. 1801007268 (Abstract).
Office Action in corresponding Taiwanese Application No. 106117499, issued Nov. 18, 2020.
European Search Report issued in related EP Application No. 20 15 236.
Search Report issued in Georgian Application No. AP 2017 14939.
Pirazzini et al., Pharmacol. Rev. 69:200-235 (2017).
Dec. 1, 2021, Office Action in corresponding Argentinian Application No. P 17 01 01464.
Dec. 8, 2021, Office Action in corresponding Chinese Application No. 201780044565.1.
Mar. 14, 2022, Office Action in corresponding South Korean Application No. 10-2018-7037095.
Dec. 18, 2020, Office Action in corresponding Macanese Application No. I/001613.
Mar. 29, 2022 Office Action in corresponding Mexican Application No. MX/a/2018/014631.
Nov. 15, 2021, Office Action in corresponding Saudi Application No. 14130/206.
Oct. 28, 2021, Office Action in corresponding Uzbek Application No. IAP 2018 0568.
Kroken et al., J. Biol. Chem. (2011), 286:26828-26837.
Chinese Journal of Aesthetic Medicine (2014), 23:1393-1397 (relevance summarized in Dec. 8, 2021, Chinese Office Action).
Aug. 24, 2022, Office Action in corresponding Indian Application No. 201817044439.
Jun. 24, 2022, Extended European Search Report in corresponding EP Application No. 21211390.6.
Feb. 15, 2023, Office Action in corresponding Canadian Application No. 3,025,437.
First Office Action, Issued Feb. 8, 2023, in corresponding Chinese Application No. 2020107426392.

* cited by examiner

SEQUENCE LISTING

```
Sequence total quantity: 7
SEQ ID NO: 1           moltype = AA  length = 1296
FEATURE                Location/Qualifiers
source                 1..1296
                       mol_type = protein
                       organism = Clostridium botulinum
SEQUENCE: 1
MPFVNKQFNY KDPVNGVDIA YIKIPNAGQM QPVKAFKIHN KIWVIPERDT FTNPEEGDLN   60
PPPEAKQVPV SYYDSTYLST DNEKDNYLKG VTKLFERIYS TDLGRMLLTS IVRGIPFWGG  120
STIDTELKVI DTNCINVIQP DGSYRSEELN LVIIGPSADI IQFECKSFGH EVLNLTRNGY  180
GSTQYIRFSP DFTFGFEESL EVDTNPLLGA GKFATDPAVT LAHELIHAGH RLYGIAINPN  240
RVFKVNTNAY YEMSGLEVSF EELRTFGGHD AKFIDSLQEN EFRLYYYNKF KDIASTLNKA  300
KSIVGTTASL QYMKNVFKEK YLLSEDTSGK FSVDKLKFDK LYKMLTEIYT EDNFVKFFKV  360
LNRKTYLNFD KAVFKINIVP KVNYTIYDGF NLRNTNLAAN FNGQNTEINN MNFTKLKNFT  420
GLFEFYKLLC VRGIITSKTK SLDKGYNKAL NDLCIKVNNW DLFFSPSEDN FTNDLNKGEE  480
ITSDTNIEAA EENISLDLIQ QYYLTFNFDN EPENISIENL SSDIIGQLEL MPNIERFPNG  540
KKYELDKYTM FHYLRAQEFE HGKSRIALTN SVNEALLNPS RVYTFFSSDY VKKVNKATEA  600
AMFLGWVEQL VYDFTDETSE VSTTDKIADI TIIIPYIGPA LNIGNMLYKD DFVGALIFSG  660
AVILLEFIPE IAIPVLGTFA LVSYIANKVL TVQTIDNALS KRNEKWDEVY KYIVTNWLAK  720
VNTQIDLIRK KMKEALENQA EATKAIINYQ YNQYTEEEKN NINFNIDDLS SKLNESINKA  780
MININKFLNQ CSVSYLMNSM IPYGVKRLED FDASLKDALL KYIYDNRGTL IGQVDRLKDK  840
VNNTLSTDIP FQLSKYVDNQ RLLSTFTEYI KNIINTSILN LRYESNHLID LSRYASKINI  900
GSKVNFDPID KNQIQLFNLE SSKIEVILKN AIVYNSMYEN FSTSFWIRIP KYFNSISLNN  960
EYTIINCMEN NSGWKVSLNY GEIIWTLQDT QEIKQRVVFK YSQMINISDY INRWIFVTIT 1020
NNRLNNSKIY INGRLIDQKP ISNLGNIHAS NNIMFKLDGC RDTHRYIWIK YFNLFDKELN 1080
EKEIKDLYDN QSNSGILKDF WGDYLQYDKP YYMLNLYDPN KYVDVNNVGI RGYMYLKGPR 1140
GSVMTTNIYL NSSLYRGTKF IIKKYASGNK DNIVRNNDRV YINVVVKNKE YRLATNASQA 1200
GVEKILSALE IPDVGNLSQV VVMKSKNDQG ITNKCKMNLQ DNNGNDIGFI GFHQFNNIAK 1260
LVASNWYNRQ IERSSRTLGC SWEFIPVDDG WGERPL                           1296

SEQ ID NO: 2           moltype = AA  length = 1291
FEATURE                Location/Qualifiers
source                 1..1291
                       mol_type = protein
                       organism = Clostridium botulinum
SEQUENCE: 2
MPVTINNFNY NDPIDNNNII MMEPPFARGT GRYYKAFKIT DRIWIIPERY TFGYKPEDFN   60
KSSGIFNRDV CEYYDPDYLN TNDKKNIFLQ TMIKLFNRIK SKPLGEKLLE MIINGIPYLG  120
DRRVPLEEFN TNIASVTVNK LISNPGEVER KKGIFANLII FGPGPVLNEN ETIDIGIQNH  180
FASREGFPGI MQMKFCPEYV SVFNNVQENK GASIFNRRGY FSDPALILMH ELIHVLHGLY  240
GIKVDDLPIV PNEKKFFMQS TDAIQAEELY TFGGQDPSII TPSTDKSIYD KVLQNFRGIV  300
DRLNKVLVCI SDPNININIY KNKFKDKYKF VEDSEGKYSI DVESFDKLYK SLMFGFTETN  360
IAENYKIKTR ASYFSDSLPP VKIKNLLDNE IYTIEEGFNI SDKDMEKEYR GQNKAINKQA  420
YEEISKEHLA VYKIQMCKSV KAPGICIDVD NEDLFFIADK NSFSDDLSKN ERIEYNTQSN  480
YIENDFPINE LILDTDLISK IELPSENTES LTDFNVDVPV YEKQPAIKKI FTDENTIFQY  540
LYSQTFPLDI RDISLTSSFD DALLFSNKVY SFFSMDYIKT ANKVVEAGLF AGWVKQIVND  600
FVIEANKSNT MDKIADISLI VPYIGLALNV GNETAKGNFE NAFEIAGASI LLEFIPELLI  660
PVVGAFLLES YIDNKNKIIK TIDNALTKRN EKWSDMVGLI VAQWLSTVNT QFYTIKEGMY  720
KALNYQAQAL EEIIKRYNI YSEKEKSNIN IDFNDINSKL NEGINQAIDN INNFINGCSV  780
SYLMKKMIPL AVEKLLDFDN TLKKNLLNYI DENKLYLIGS AEYEKSKVNK YLKTIMPFDL  840
SIYTNDTILI EMFNKYNSEI LNNIILNLRY KDNNLIDLSG YGAKVEVYDG VELNDKNQFK  900
LTSSANSKIR VTQNQNIIFN SVFLDFSVSF WIRIPKYKND GIQNYIHNEY TIINCMKNNS  960
GWKISIRGNR IIWTLIDING KTKSVFFEYN IREDISEYIN RWFFVTITNN LNNAKIYING 1020
KLESNTDIKD IREVIANGEI IFKLDGDIDR TQFIWMKYFS IFNTELSQSN IEERYKIQSY 1080
SEYLKDFWGN PLMYNKEYYM FNAGNKNSYI KLKKDSPVGE ILTRSKYNQN SKYINYRDLY 1140
IGEKFIIRRK SNSQSINDDI VRKEDYIYLD FFNLNQEWRV YTYKYFKKEE EKLFLAPISD 1200
SDEFYNTIQI KEYDEQPTYS CQLLFKKDEE STDEIGLIGI HRFYESGIVF EEYKDYFCIS 1260
KWYLKEVKRK PYNLKLGCNW QFIPKDEGWT E                                1291

SEQ ID NO: 3           moltype = AA  length = 1291
FEATURE                Location/Qualifiers
source                 1..1291
                       mol_type = protein
                       organism = Clostridium botulinum
SEQUENCE: 3
MPITINNFNY SDPVDNKNIL YLDTHLNTLA NEPEKAFRIT GNIWVIPDRF SRNSNPNLNK   60
PPRVTSPKSG YYDPNYLSTD SDKDPFLKEI IKLFKRINSR EIGEELIYRL STDIPFPGNN  120
NTPINTFDFD VDFNSVDVKT RQGNNWVKTG SINPSVIITG PRENIIDPET STFKLTNNTF  180
AAQEGFGALS IISISPRFML TYSNATNDVG EGRFSKSEFC MDPILILMHE LNHAMHNLYG  240
IAIPNDQTIS SVTSNIFYSQ YNVKLEYAEI YAFGGPTIDL IPKSARKYFE EKALDYYRSI  300
AKRLNSITTA NPSSFNKYIG EYKQKLIRKY RFVVESSGEV TVNRNKFVEL YNELTQIFTE  360
FNYAKIYNVQ NRKIYLSNVY TPVTANILDD NVYDIQNGFN IPKSNLNVLF MGQNLSRNPA  420
LRKVNPENML YLFTKFCHKA IDGRSLYNKT LDCRELLVKN TDLPFIGDIS DVKTDIFLRK  480
DINEETEVIY YPDNVSVDQV ILSKNTSEHG QLDLLYPSID SESEILPGEN QVFYDNRTQN  540
VDYLNSYYYL ESQKLSDNVE DFTFTRSIEE ALDNSAKVYT YPPTLANKVN AGVQGGLFLM  600
WANDVVEDFT TNILRKDTLD KISDVSAIIP YIGPALNISN SVRRGNFTEA FAVTGVTILL  660
EAFPEFTIPA LGAFVIYSKV QERNEIIKTI DNCLEQRIKR WKDSYEWMMG TWLSRIITQF  720
NNISYQMYDS LNYQAGAIKA KIDLEYKKYS GSDKENIKSQ VENLKNSLDV KISEAMNNIN  780
```

```
KFIRECSVTY LFKNMLPKVI DELNEFDRNT KAKLINLIDS HNIILVGEVD KLKAKVNNSF  840
QNTIPFNIFS YTNNSLLKDI INEYFNNIND SKILSLQNRK NTLVDTSGYN AEVSEEGDVQ  900
LNPIFPFDFK LGSSGEDRGK VIVTQNENIV YNSMYESFSI SFWIRINKWV SNLPGYTIID  960
SVKNNSGWSI GIISNFLVFT LKQNEDSEQS INFSYDISNN APGYNKWFFV TVTNNMMGNM 1020
KIYINGKLID TIKVKELTGI NFSKTITFEI NKIPDTGLIT SDSDNINMWI RDFYIFAKEL 1080
DGKDINILFN SLQYTNVVKD YWGNDLRYNK EYYMVNIDYL NRYMYANSRQ IVFNTRRNNN 1140
DFNEGYKIII KRIRGNTNDT RVRGGDILYF DMTINNKAYN LFMKNETMYA DNHSTEDIYA 1200
IGLREQTKDI NDNIIFQIQP MNNTYYYASQ IFKSNFNGEN ISGICSIGTY RFRLGGDWYR 1260
HNYLVPTVKQ GNYASLLEST STHWGFVPVS E                              1291

SEQ ID NO: 4           moltype = AA   length = 1276
FEATURE                Location/Qualifiers
source                 1..1276
                       mol_type = protein
                       organism = Clostridium botulinum
SEQUENCE: 4
MTWPVKDFNY SDPVNDNDIL YLRIPQNKLI TTPVKAFMIT QNIWVIPERF SSDTNPSLSK   60
PPRPTSKYQS YYDPSYLSTD EQKDTFLKGI IKLFKRINER DIGKKLINYL VVGSPFMGDS  120
STPEDTFDFT RHTTNIAVEK FENGSWKVTN IITPSVLIFG PLPNILDYTA SLTLQGQQSN  180
PSFEGFGTLS ILKVAPEFLL TFSDVTSNQS SAVLGKSIFC MDPVIALMHE LTHSLHQLYG  240
INIPSDKRIR PQVSEGFFSQ DGPNVQFEEL YTFGGLDVEI IPQIERSQLR EKALGHYKDI  300
AKRLNNINKT IPSSWISNID KYKKIFSEKY NFDKDNTGNF VVNIDKFNSL YSDLTNVMSE  360
VVYSSQYNVK NRTHYFSRHY LPVFANILDD NIYTIRDGFN LTNKGFNIEN SGQNIERNPA  420
LQKLSSESVV DLFTKVCLRL TKNSRDDSTC IKVKNNRLPY VADKDSISQE IFENKIITDE  480
TNVQNYSDKF SLDESILDGQ VPINPEIVDP LLPNVNMEPL NLPGEEIVFY DDITKYVDYL  540
NSYYYLESQK LSNNVENITL TTSVEEALGY SNKIYTFLPS LAEKVNKGVQ AGLFLNWANE  600
VVEDFTTNIM KKDTLDKISD VSVIIPYIGP ALNIGNSALR GNFNQAFATA GVAFLLEGFP  660
EFTIPALGVF TFYSSIQERE KIIKTIENCL EQRVKRWKDS YQWMVSNWLS RITTQFNHIN  720
YQMYDSLSYQ ADAIKAKIDL EYKKYSGSDK ENIKSQVENL KNSLDVKISE AMNNINKFIR  780
ECSVTYLFKN MLPKVIDELN KFDLRTKTEL INLIDSHNII LVGEVDRLKA KVNESFENTM  840
PFNIFSYTNN SLLKDIINEY FNSINDSKIL SLQNKKNALV DTSGYNAEVR VGDNVQLNTI  900
YTNDFKLSSS GDKIIVNLNN NILYSAIYEN SSVSFWIKIS KDLTNSHNEY TIINSIEQNS  960
GWKLCIRNGN IEWILQDVNR KYKSLIFDYS ESLSHTGYTN KWFFVTITNN IMGYMKLYIN 1020
GELKQSQKIE DLDEVKLDKT IVFGIDENID ENQMLWIRFP NIFSKELSNE DINIVYEGQI 1080
LRNVIKDYWG NPLKFDTEYY IINDNYIDRY IAPESNVLVL VQYPDRSKLY TGNPITIKSV 1140
SDKNPYSRIL NGDNIILHML YNSRKYMIIR DTDTIYATQG GECSQNCVYA LKLQSNLGNY 1200
GIGIFSIKNI VSKNKYCSQI FSSFRENTML LADIYKPWRF SFKNAYTPVA VTNYETKLLS 1260
TSSFWKFISR DPGWVE                                               1276

SEQ ID NO: 5           moltype = AA   length = 1252
FEATURE                Location/Qualifiers
source                 1..1252
                       mol_type = protein
                       organism = Clostridium botulinum
SEQUENCE: 5
MPKINSFNYN DPVNDRTILY IKPGGCQEFY KSFNIMKNIW IIPERNVIGT TPQDFHPPTS   60
LKNGDSSYYD PNYLQSDEEK DRFLKIVTKI FNRINNNLSG GILLEELSKA NPYLGNDNTP  120
DNQFHIGDAS AVEIKFSNGS QDILLPNVII MGAEPDLFET NSSNISLRNN YMPSNHGFGS  180
IAIVTFSPEY SFRFNDNSMN EFIQDPALTL MHELIHSLHG LYGAKGITTK YTITQKQNPL  240
ITNIRGTNIE EFLTFGGTDL NIITSAQSND IYTNLLADYK KIASKLSKVQ VSNPLLNPYK  300
DVFEAKYGLD KDASGIYSVN INKFNDIFKK LYSFTEFDLA TKFQVKCRQT YIGQYKYFKL  360
SNLLNDSIYN ISEGYNINNL KVNFRGQNAN LNPRIITPIT GRGLVKKIIR FCKNIVSVKG  420
IRKSICIEIN NGELFFVASE NSYNDDNINT PKEIDDVTS NNNYENDLDQ VILNFNSESA  480
PGLSDEKLNL TIQNDAYIPK YDSNGTSDIE QHDVNELNVF FYLDAQKVPE GENNVNLTSS  540
IDTALLEQPK IYTFFSSEFI NNVNKPVQAA LFVSWIQQVL VDFTTEANQK STVDKIADIS  600
IVVPYIGLAL NIGNEAQKGN FKDALELLGA GILLEFEPEL LIPTILVFTI KSFLGSSDNK  660
NKVIKAINNA LKERDEKWKE VYSFIVSNWM TKINTQFNKR KEQMYQALQN QVNAIKTIIE  720
SKYNSYTLEE KNELTNKYDI KQIENELNQK VSIAMNNIDR FLTESSISYL MKLINEVKIN  780
KLREYDENVK TYLLNYIIQH GSILGESQQE LNSMVTDTLN NSIPFKLSSY TDDKILISYF  840
NKFFKRIKSS SVLNMRYKND KYVDTSGYDS NININGDVYK YPTNKNQFGI YNDKLSEVNI  900
SQNDYIIYDN KYKNFSISFW VRIPNYDNKI VNVNNEYTII NCMRDNNSGW KVSLNHNEII  960
WTLQDNAGIN QKLAFNYGNA NGISDYINKW IFVTITNDRL GDSKLYINGN LIDQKSILNL 1020
GNIHVSDNIL FKIVNCSYTR YIGIRYFNIF DKELDETEIQ TLYSNEPNTN ILKDFWGNLL 1080
LYDKEYYLLN VLKPNNFIDR RKDSTLSINN IRSTILLANR LYSGIKVKIQ RVNNSSTNDN 1140
LVRKNDQVYI NFVASKTHLF PLYADTATTN KEKTIKISSS GNRFNQVVVM NSVGNNCTMN 1200
FKNNNGNNIG LLGFKADTVV ASTWYYTHMR DHTNSNGCFW NFISEEHGWQ EK         1252

SEQ ID NO: 6           moltype = AA   length = 1274
FEATURE                Location/Qualifiers
source                 1..1274
                       mol_type = protein
                       organism = Clostridium botulinum
SEQUENCE: 6
MPVAINSFNY NDPVNDDTIL YMQIPYEEKS KKYYKAFEIM RNVWIIPERN TIGTNPSDFD   60
PPASLKNGSS AYYDPNYLTT DAEKDRYLKT TIKLFKRINS NPAGKVLLQE ISYAKPYLGN  120
DHTPIDEFSP VTRTTSVNIK LSTNVESSML LNLLVLGAGP DIFESCCYPV RKLIDPDVVY  180
DPSNYGFGSI NIVTFSPEYE YTFNDISGGH NSSTESFIAD PAISLAHELI HALHGLYGAR  240
GVTYEETIEV KQAPLMIAEK PIRLEEFLTF GGQDLNIITS AMKEKIYNNL LANYEKIATR  300
LSEVNSAPPE YDINEYKDYF QWKYGLDKNA DGSYTVNENK FNEIYKKLYS FTESDLANKF  360
```

```
KVKCRNTYFI KYEFLKVPNL LDDDIYTVSE GFNIGNLAVN NRGQSIKLNP KIIDSIPDKG  420
LVEKIVKFCK SVIPRKGTKA PPRLCIRVNN SELFFVASES SYNENDINTP KEIDDTTNLN  480
NNYRNNLDEV ILDYNSQTIP QISNRTLNTL VQDNSYVPRY DSNGTSEIEE YDVVDFNVFF  540
YLHAQKVPEG ETNISLTSSI DTALLEESKD IFFSSEFIDT INKPVNAALF IDWISKVIRD  600
FTTEATQKST VDKIADISLI VPYVGLALNI IIEAEKGNFE EAFELLGVGI LLEFVPELTI  660
PVILVFTIKS YIDSYENKNK AIKAINNSLI EREAKWKEIY SWIVSNWLTR INTQFNKRKE  720
QMYQALQNQV DAIKTAIEYK YNNYTSDEKN RLESEYNINN IEEELNKKVS LAMKNIERFM  780
TESSISYLMK LINEAKVGKL KKYDNHVKSD LLNYILDHRS ILGEQTNELS DLVTSTLNSS  840
IPFELSSYTN DKILIIYFNR LYKKIKDSSI LDMRYENNKF IDISGYGSNI SINGNVYIYS  900
TNRNQFGIYN SRLSEVNIAQ NNDIIYNSRY QNFSISFWVR IPKHYKPMNH NREYTIINCM  960
GNNNSGWKIS LRTVRDCEII WTLQDTSGNK ENLIFRYEEL NRISNYINKW IFVTITNNRL 1020
GNSRIYINGN LIVEKSISNL GDIHVSDNIL FKIVGCDDET YVGIRYFKVF NTELDKTEIE 1080
TLYSNEPDPS ILKNYWGNYL LYNKKYYLFN LLRKDKYITL NSGILNINQQ RGVTEGSVFL 1140
NYKLYEGVEV IIRKNGPIDI SNTDNFVRKN DLAYINVVDR GVEYRLYADT KSEKEKIIRT 1200
SNLNDSLGQI IVMDSIGNNC TMNFQNNNGS NIGLLGFHSN NLVASSWYYN NIRRNTSSNG 1260
CFWSSISKEN GWKE                                                  1274

SEQ ID NO: 7          moltype = AA  length = 1297
FEATURE               Location/Qualifiers
source                1..1297
                      mol_type = protein
                      organism = Clostridium botulinum
SEQUENCE: 7
MPVNIKNFNY NDPINNDDII MMEPFNDPGP GTYYKAFRII DRIWIVPERF TYGFQPDQFN   60
ASTGVFSKDV YEYYDPTYLK TDAEKDKFLK TMIKLFNRIN SKPSGQRLLD MIVDAIPYLG  120
NASTPPDKFA ANVANVSINK KIIQPGAEDQ IKGLMTNLII FGPGPVLSDN FTDSMIMNGH  180
SPISEGFGAR MMIRFCPSCL NVFNNVQENK DTSIFSRRAY FADPALTLMH ELIHVLHGLY  240
GIKISNLPIT PNTKEFFMQH SDPVQAEELY TFGGHDPSVI SPSTDMNIYN KALQNFQDIA  300
NRLNIVSSAQ GSGIDISLYK QIYKNKYDFV EDPNGKYSVD KDKFDKLYKA LMFGFTETNL  360
AGEYGIKTRY SYFSEYLPPI KTEKLLDNTI YTQNEGFNIA SKNLKTEFNG QNKAVNKEAY  420
EEISLEHLVI YRIAMCKPVM YKNTGKSEQC IIVNNEDLFF IANKDSFSKD LAKAETIAYN  480
TQNNTIENNF SIDQLILDND LSSGIDLPNE NTEPFTNFDD IDIPVYIKQS ALKKIFVDGD  540
SLFEYLHAQT FPSNIENLQL TNSLNDALRN NNKVYTFFST NLVEKANTVV GASLFVNWVK  600
GVIDDFTSES TQKSTIDKVS DVSIIIPYIG PALNVGNETA KENFKNAFEI GGAAILMEFI  660
PELIVPIVGF FTLESYVGNK GHIIMTISNA LKKRDQKWTD MYGLIVSQWL STVNTQFYTI  720
KERMYNALNN QSQAIEKIIE DQYNRYSEED KMNINIDFND IDFKLNQSIN LAINNIDDFI  780
NQCSISYLMN RMIPLAVKKL KDFDDNLKRD LLEYIDTNEL YLLDEVNILK SKVNRHLKDS  840
IPFDLSLYTK DTILIQVFNN YISNISSNAI LSLSYRGGRL IDSSGYGATM NVGSDVIFND  900
IGNGQFKLNN SENSNITAHQ SKFVVYDSMF DNFSINFWVR TPKYNNNDIQ TYLQNEYTII  960
SCIKNDSGWK VSIKGNRIIW TLIDVNAKSK SIFFEYSIKD NISDYINKWF SITITNDRLG 1020
NANIYINGSL KKSEKILNLD RINSSNDIDF KLINCTDTTK FVWIKDFNIF GRELNATEVS 1080
SLYWIQSSTN TLKDFWGNPL RYDTQYYLFN QGMQNIYIKY FSKASMGETA PRTNFNNAAI 1140
NYQNLYLGLR FIIKKASNSR NINNDNIVRE GDYIYLNIDN ISDESYRVYV LVNSKEIQTQ 1200
LFLAPINDDP TFYDVLQIKK YYEKTTYNCQ ILCEKDTKTF GLFGIGKFVK DYGYVWDTYD 1260
NYFCISQWYL RRISENINKL RLGCNWQFIP VDEGWTE                         1297
```

LIQUID NEUROTOXIN FORMULATION STABILIZED WITH TRYPTOPHAN OR TYROSINE

CROSS-REFERENCE TO RELATED APPLICATIONS

The present application is a continuation of U.S. application Ser. No. 18/173,991, filed Feb. 24, 2023, which is a continuation of U.S. application Ser. No. 17/304,888, filed Jun. 28, 2021, which is a continuation of Ser. No. 16/304,986, which is a U.S. national stage filing of International Application No. PCT/EP2017/062785, filed May 26, 2017, which claims the priority benefit of International Application No. PCT/EP2016/062085, filed May 27, 2016, each of which is hereby incorporated by reference in its entirety.

REFERENCE TO SEQUENCE LISTING

The present application contains a Sequence Listing which that been filed electronically in XML format and is hereby incorporated by reference in its entirety. The XML copy, created or Sep. 28, 2023, is named 394760SeqList.xml and is 16,056 bytes in size.

FIELD OF THE INVENTION

The present invention relates to animal protein free liquid neurotoxin formulations. In particular, the present invention relates to animal protein free liquid botulinum neurotoxin formulations stabilized with non proteinaceous excipients.

The neurotoxin formulations described herein are suitable for use in therapy and in particular for administration to a patient to achieve a desired therapeutic or aesthetic effect.

BACKGROUND OF THE INVENTION

Clostridial neurotoxins naturally produced by clostridial strains are the most toxic biological agents known to date and at the same time are powerful tools for the treatment of a number of neuromuscular and endocrine disorders, including cervical dystonia, spasticity, blepharospasm, hyperhidrosis or sialorrhea. They also find uses in the aesthetic field for the smoothing of wrinkles.

In order to be suitable for use as a pharmaceutical product, a neurotoxin composition must be such that it can be stored without significant loss of neurotoxin activity.

In all currently approved formulations of botulinum neurotoxins, an animal (including human) protein, usually human serum albumin (HSA), is used as a stabiliser.

The presence of animal proteins such as HSA in pharmaceutical compositions is however undesirable because of the risk, even if low, of unwillingly transmitting animal borne infectious agents such as prions to a patient.

Animal protein free botulinum toxin formulations have been disclosed in the art. For example, WO0158472 describes lyophilized compositions in which a polysaccharide, such as 2-hydroxyethyl starch is used to stabilize a botulinum toxin. WO2005007185 describes compositions in which a surface active substance, and a mixture of at least two amino acids selected from Glu and Gln or Asp and Asn are used to stabilize a botulinum toxin.

Most prior art formulations are however not stable in liquid form and are therefore stored in lyophilized or freeze-dried form. Such formulations need to be reconstituted by the physician in a sterile saline solution before administration to a patient. This reconstitution step is associated with a loss of physician time, a risk of a dilution error and also a risk of contamination during the reconstitution process. The botulinum toxin provider must also train the physicians in order to ensure that the reconstitution step is performed adequately.

Liquid formulations are therefore advantageous as they obviate the loss of time for the physician, the risk of a dilution error, the contamination risk and the need for providing training for the provider.

Liquid HSA-free formulations are described for example in WO2006005910 which discloses liquid botulinum toxin formulations comprising a surfactant, sodium chloride and a disaccharide. WO2009008595 discloses liquid botulinum toxin formulations comprising polysorbate 20 and methionine.

It is an objective of the present invention to provide advantageous liquid animal protein free botulinum neurotoxin formulations, which are suitable for storage and for use in therapy. In particular, the stabilizing formulation should maintain product stability, be free of animal proteins and also be suitable for stabilising a neurotoxin which is free of complexing proteins.

SUMMARY OF THE INVENTION

A first aspect of the present invention is a liquid composition comprising or consisting essentially of a proteinaceous neurotoxin, a surfactant, an amino acid selected from tryptophan and tyrosine, a buffer comprising sodium, chloride and phosphate ions, which has a pH between 5.5 and 8, which is stable over time and which is free of animal derived proteins.

Another aspect is the use of the liquid compositions according to the invention in therapy and/or in cosmetics.

A further aspect of the present invention is the use of an amino acid selected from tryptophan and tyrosine to protect a proteinaceous neurotoxin from degradation in a liquid composition which is free of animal derived proteins.

DETAILED DESCRIPTION OF THE INVENTION

A first aspect of the present invention is a liquid composition comprising or consisting essentially of a proteinaceous neurotoxin, a surfactant, an amino acid selected from tryptophan and tyrosine, a buffer comprising sodium, chloride and phosphate ions, which has a pH between 5.5 and 8, which is stable over time and which is free of animal derived proteins.

"Animal protein free" is to be understood as comprising no protein of animal, including human, origin.

A neurotoxin is a substance that targets a nerve cell and affects a neurological function. Proteinaceous neurotoxins include botulinum toxins (BoNT) and tetanus toxin (TeNT). Preferably, the proteinaceous neurotoxin is a botulinum neurotoxin.

Botulinum neurotoxins are 150 kDa metalloproteases that consist in their active form of a 50 kDa light chain (L) and a 100 kDa heavy chain (H) linked by a disulfide bridge. The L chain is a zinc-protease which intracellularly cleaves one of the SNARE (Soluble NSF Attachment Protein REceptor) proteins involved in vesicle mediated neurotransmitter release, thereby disrupting neurotransmitter mediated mechanisms. The heavy chain encompasses two domains: an N-terminal 50 kDa translocation domain ($H_N$), and a C-terminal 50 kDa receptor-binding domain ($H_C$). The $H_C$ domain of a botulinum neurotoxin comprises two distinct structural features that are referred to as the $H_{CC}$ and $H_{CN}$ domains. Amino acid residues involved in receptor binding are believed to be primarily located in the domain.

Botulinum neurotoxins have been classified in 7 antigenically distinct serotypes (A to G). Exemplary amino acid sequences for each serotype are provided herein as SEQ ID NO 1 to 7.

For each of the sequences, the different domains can for example be as follow.

| Serotype | L chain | $H_N$ domain | $H_{CN}$ domain | $H_{CC}$ domain |
|---|---|---|---|---|
| BoNT/A (SEQ ID NO: 1) | 1-448 | 449-871 | 872-1110 | 1111-1296 |
| BoNT/B (SEQ ID NO: 2) | 1-440 | 441-858 | 859-1097 | 1098-1291 |
| BoNT/C (SEQ ID NO: 3) | 1-441 | 442-866 | 867-1111 | 1112-1291 |
| BoNT/D (SEQ ID NO: 4) | 1-445 | 446-862 | 863-1098 | 1099-1276 |
| BoNT/E (SEQ ID NO: 5) | 1-422 | 423-845 | 846-1085 | 1086-1252 |
| BoNT/F (SEQ ID NO 6) | 1-439 | 440-864 | 865-1105 | 1106-1274 |
| BoNT/G (SEQ ID NO 7) | 1-441 | 442-863 | 864-1105 | 1106-1297 |

The skilled person will appreciate that there can be some variation in each of the botulinum neurotoxin domains.

BoNTs act for example on neuromuscular nerve junctions by preventing release of acetylcholine and thereby preventing muscular contraction. Nerve terminal intoxication is reversible and its duration varies for different BoNT serotypes.

Natural BoNTs are produced by Clostridium botulinum, and other Clostridial species such as *C. butyricum, C. baratii* and *C. argentinense* as part of multi-protein complexes that protect the neurotoxin from proteolytic degradation. By "botulinum neurotoxin in complex form" is meant a botulinum neurotoxin and one or more of the proteins which are part in nature of such multi-protein complexes (neurotoxin-associated proteins or "NAPs"). NAPs include non-toxic non-hemagglutinin (NTNH) protein and hemagglutinin proteins (HA-17, HA-33, and HA-70). By "high purity botulinum neurotoxin" is meant a botulinum neurotoxin essentially free of NAPs.

According to an embodiment of the invention, the botulinum neurotoxin is a botulinum neurotoxin in complex form. According to another embodiment, the botulinum neurotoxin is a high purity botulinum neurotoxin.

Method for producing BoNTs through culture of natural clostridial strains and purifying them either in complex form or high purity form are well known in the art and are described example in Pickett, Andy. "Botulinum toxin as a clinical product: manufacture and pharmacology." Clinical Applications of Botulinum Neurotoxin. Springer New York, 2014. 7-49.

High purity or essentially pure botulinum neurotoxin can be obtained from a protein complex comprising botulinum toxin for example according to the method described in Current topics in Microbiology and Immunology (1995), 195, p. 151-154.

Alternatively, high purity botulinum neurotoxin can be produced by recombinant expression of a BoNT gene in a heterologous host such as *E. coli* and purified therefrom.

Preferably, the proteinaceous neurotoxin is a botulinum neurotoxin. According to an embodiment of the invention, the botulinum neurotoxin is a botulinum neurotoxin in complex form. According to another embodiment, the botulinum neurotoxin is a high purity botulinum neurotoxin.

According to an embodiment of the invention, the botulinum neurotoxin is a botulinum neurotoxin purified from its natural clostridial strain. According to another embodiment, botulinum neurotoxin is a botulinum neurotoxin produced recombinantly in a heterologous host such as *E. coli*.

According to the present invention, the Botulinum neurotoxin can be a BoNT of serotype A, B, C, D, E, F or G.

According to the present invention, a botulinum neurotoxin can be a modified botulinum neurotoxin. According to the present invention, a "modified BoNT" is a BoNT which has an amino acid sequence which has at least 50% sequence identity with SEQ ID NO 1, 2, 3, 4, 5, 6 or 7. Preferably, a modified BoNT has an amino acid sequence which has at least 60%, 70%, 80%, 85%, 90%, 95%, 96%, 97%, 98% or 99% sequence identity with SEQ ID NO 1, 2, 3, 4, 5, 6 or 7. Preferably, a modified BoNT is a BoNT whose amino acid sequence differs from SEQ ID NO 1, 2, 3, 4, 5, 6 or 7 by less than 600, 400, 200, 150, 100, 50 or 20 amino acid substitutions, deletions or additions, for example by 10, 9, 8, 7, 6, 5, 4, 3, 2 or 1 amino acid substitutions, deletions or additions.

According to the present invention, a recombinant botulinum neurotoxin can be a chimeric botulinum neurotoxin. According to the present invention, a "chimeric BoNT" is constituted by an L, $H_N$, $H_{CN}$, and $H_{CC}$ domain which do not all belong to the same serotype. For example a chimeric BoNT can consist of an L chain from one serotype and a full H chain ($H_N$, $H_{CN}$, and $H_{CC}$ domains) from a different serotype. A chimeric BoNT can also consist of an L chain and an $H_N$ domain ("$LH_N$") from one serotype and an $H_C$ domain ($H_{CN}$ and $H_{CC}$) from a different serotype. A chimeric BoNT can also consist of an L chain and $H_N$ and $H_{CN}$ domains ("extended $LH_N$") from one serotype and an $H_{CC}$ domain from a different serotype.

According to the invention a Light chain domain (L) can have an amino acid sequence which has at least 50%, preferably at least 60%, 70%, 80%, 90% or 95% sequence identity to one of the following amino acid sequences and which retains the ability to cleave one of the SNARE proteins involved in vesicle mediated neurotransmitter release:

Amino acid 1-448 of SEQ ID NO:1
Amino acid 1-440 of SEQ ID NO:2
Amino acid 1-441 of SEQ ID NO:3
Amino acid 1-445 of SEQ ID NO:4
Amino acid 1-422 of SEQ ID NO:5
Amino acid 1-439 of SEQ ID NO:6
Amino acid 1-441 of SEQ ID NO:7

According to the invention an $H_N$ domain can have an amino acid sequence which has at least 50%, preferably at least 60%, 70%, 80%, 90% or 95% sequence identity to one of the following amino acid sequences and which retains a translocation ability:

Amino acid 449-871 of SEQ ID NO:1
Amino acid 441-858 of SEQ ID NO:2
Amino acid 442-866 of SEQ ID NO:3
Amino acid 446-862 of SEQ ID NO:4
Amino acid 423-845 of SEQ ID NO:5
Amino acid 440-864 of SEQ ID NO:6
Amino acid 442-863 of SEQ ID NO:7

According to the invention an $H_C$ domain can have an amino acid sequence which has at least 50%, preferably at least 60%, 70%, 80%, 90% or 95% sequence identity to one of the following amino acid sequences and which retains the ability to bind to a neuromuscular cell:

Amino acid 872-1296 of SEQ ID NO:1
Amino acid 859-1291 of SEQ ID NO:2
Amino acid 867-1291 of SEQ ID NO:3
Amino acid 863-1276 of SEQ ID NO:4
Amino acid 846-1252 of SEQ ID NO:5

Amino acid 865-1274 of SEQ ID NO:6
Amino acid 864-1297 of SEQ ID NO:7

According to the invention an $H_{CC}$ domain can have an amino acid sequence which has at least 50%, preferably at least 60%, 70%, 80%, 90% or 95% sequence identity to one of the following amino acid sequences and which retains the ability to bind to a neuromuscular cell:

Amino acid 1111-1296 of SEQ ID NO:1
Amino acid 1098-1291 of SEQ ID NO:2
Amino acid 1112-1291 of SEQ ID NO:3
Amino acid 1099-1276 of SEQ ID NO:4
Amino acid 1086-1252 of SEQ ID NO:5
Amino acid 1106-1274 of SEQ ID NO:6
Amino acid 1106-1297 of SEQ ID NO:7

The above-identified reference sequences should be considered as a guide, as slight variations may occur according to sub-serotypes.

The "percent sequence identity" between two or more nucleic acid or amino acid sequences is a function of the number of identical nucleotides/amino acids at identical positions shared by the aligned sequences. Thus, % identity may be calculated as the number of identical nucleotides/amino acids at each position in an alignment divided by the total number of nucleotides/amino acids in the aligned sequence, multiplied by 100. Calculations of % sequence identity may also take into account the number of gaps, and the length of each gap that needs to be introduced to optimize alignment of two or more sequences.

Sequence comparisons and the determination of percent identity between two or more sequences can be carried out using specific mathematical algorithms, such as BLAST, which will be familiar to a skilled person.

Surfactants (or surface active agents) are compounds that are able to lower the surface tension between a liquid and a solid or between two liquids. Surfactants can be non-ionic, anionic, cationic or amphoteric. In the compositions according to the invention, the surfactant is preferably a non-ionic surfactant. Non-ionic surfactants include Polyoxyethylene glycol alkyl ethers, such as Octaethylene glycol monododecyl ether or Pentaethylene glycol monododecyl ether; Polyoxypropylene glycol alkyl ethers; Glucoside alkyl ethers, such as Decyl glucoside, Lauryl glucoside or Octyl glucoside; Polyoxyethylene glycol octylphenol ethers, such as Triton X-100; Polyoxyethylene glycol alkylphenol ethers, such as Nonoxynol-9; Glycerol alkyl esters, such as Glyceryl laurate; Polyoxyethylene glycol sorbitan alkyl esters, such as Polysorbates; Sorbitan alkyl esters, such as Spans; Cocamide MEA, cocamide DEA; Dodecyldimethylamine oxide; Block copolymers of polyethylene glycol and polypropylene glycol, such as Poloxamers; Polyethoxylated tallow amine (POEA).

According to a preferred embodiment, the liquid composition according to the invention comprises a non-ionic surfactant which is a polysorbate, preferably polysorbate 20 (PS20), polysorbate 60 (PS60) or polysorbate 80 (PS80). Most preferably, the non-ionic surfactant is PS80. When the surfactant is a polysorbate, its concentration is preferably from 0.001% to 15% v/v, more preferably from 0.005 to 2% v/v, more preferably still from 0.01 to 1% for example 0.01, 0.05, 0.1, 0.2, 0.5 or 1% v/v. According to one embodiment, the surfactant is PS80 at a concentration from 0.05 to 0.2% v/v, for example about 0.05, 0.06, 0.07, 0.08, 0.09, 0.10, 0.11, 0.12, 0.13, 0.14, 0.15, 0.16, 0.17, 0.18, 0.19 or 0.20% v/v.

PS20 has a density of approximately 1.1 g/mL. PS60 has a density of approximately 1.044 g/mL. PS80 has a density of approximately 1.06 to 1.09 g/mL.

Polysorbates are believed to form micelles and prevent adsorption of proteins to surfaces and protein aggregation. Without wishing to be bound by theory, it is believed that upon degradation/oxidation, polysorbates may form peroxides and acids that may have an effect on protein stability. Therefore, it is considered preferable that the concentration of polysorbate be as low as possible in the formulation of the product. It is therefore considered preferable that the concentration of polysorbate should not exceed 200 times its critical micellar concentration (CMC), more preferably it should not exceed 100, 50, 20, 10 or 5 times its CMC.

For PS20 (Mw 1227.5 g/mol), the CMC is approximatively $8 \times 10^{-5}$ M at 21° C., i.e. approximately 0.01% w/v.

For PS60 (Mw 1309 g/mol), the CMC is approximately $21 \times 10^{-6}$ M at 21° C., i.e. approximately 0.003% w/v.

For PS80 (Mw 1310 g/mol), the CMC is approximatively $12 \times 10^{-6}$ M at 21° C., i.e. approximately 0.002% w/v.

According to a preferred embodiment, the polysorbate concentration is between 1 and 200 times its CMC at a given temperature, for example about 21° C., preferably between 2 and 100 times its CMC, for example about 20 or 50 times its CMC.

The liquid composition according to the invention comprises an amino acid which is tryptophan or tyrosine. Without willing to be bound by theory, it is hypothesized that tryptophan or tyrosine can prevent oxidation of the active protein which would render it non-functional. Indeed, it is thought that the amino acid added in molar excess over the neurotoxin will be oxidized in the first place, saving the neurotoxin. It is also hypothesized that tryptophan or tyrosine can neutralize reactive degradation products of surfactants such as polysorbates.

Preferably the amino acid is tryptophan. More preferably, the amino acid is L-tryptophan.

The amino acid concentration is preferably from about 0.1 to 5 mg/mL, more preferably between 0.1 and 5 mg/mL, from 0.25 and 3 mg/mL for example about 0.25, 0.5, 1, 1.5, 2 or 3 mg/mL.

The composition according to the invention comprises a buffer which comprises sodium, chloride and phosphate ions. The inventors indeed surprisingly found that buffers without sodium, chloride and phosphate ions lowered the stability of the toxin. Preferably the buffer also comprises potassium ions.

The buffer can for example be obtained by combining sodium chloride, potassium chloride and sodium phosphate salts. The sodium chloride concentration is preferably from 10 to 500 mM, preferably from about 25 to 300 mM, for example about 25, 50, 75, 100, 140, 150, 200, 250 or 300 mM.

The sodium phosphate concentration is preferably from 1 to 100 mM, preferably from 2 to 50 mM, for example about 2, 5, 10, 20, 30, 40 or 50 mM.

The potassium chloride concentration is preferably from 1 to 50 mM, preferably from 1 to 10 mM for example about 1, 2, 3, 4, 5 or 10 mM.

The composition according to the invention has a pH between 5.5 and 8. According to a preferred embodiment, the pH is between 6.0 and 7.5, for example about 6.3, 6.35, 6.4, 6.45, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5. Preferably the pH is within one unit from physiological pH (which is around 7.4).

The composition according to the invention is liquid. The composition preferably comprises an aqueous diluent, more preferably water, for example sterile water, water for injection, purified water, sterile water for injection.

Preferably the formulation is isotonic and is suitable for injection to a patient, in particular a human patient.

The quantity of botulinum neurotoxin is commonly expressed in mouse LD50 (lethal dose 50) units, defined as the median lethal intraperitoneal dose in mice.

The mouse LD50 (MLD50) unit for botulinum toxins is not a standardised unit. Indeed, assays used by different manufacturers of marketed toxins differ in particular in the choice of dilution buffer. For example the test used for Dysport® uses gelatine phosphate buffer, whereas the assay used for BOTOX® uses saline as a diluent. It is believed that gelatine buffers protect the toxin at the high dilutions used in LD50 assays. In contrast the use of saline as a diluent is thought to lead to some loss of potency. This could explain why when tested with the Dysport® assay, one BOTOX® unit is equivalent to approximately three units of Dysport (Straughan, D. W., 2006, ATLA 34(3), 305-313; Hambleton and Pickett, Hambleton, P., and A. M. Pickett., 1994, Journal of the Royal Society of Medicine 87.11: 719).

Preferably, the dilution buffer used to determine the mouse LD50 is a gelatine phosphate buffer. For example, the mouse LD50 can be determined as described in Hambleton, P. et al. Production, purification and toxoiding of Clostridium botulinum type A toxin. Eds. G. E. Jr Lewis, and P. S. Angel. Academic Press, Inc., New York, USA, 1981, p. 248. Briefly, botulinum toxin samples are serially diluted in 0.2% (w/v) gelatine 0.07M Na2HPO4 buffer at pH 6.5. Groups of mice (eg 4 to 8 mice per group) weighing about 20 g are injected intraperitoneally with a sample of diluted toxin (for example 0.5 ml per animal). Dilution groups, for example 5 dilution groups, are selected to span the 50% lethality dose. The mice are observed for up to 96 hours and the mouse lethal dose 50 (MLD50) is estimated.

The composition according to the invention preferably comprises from 4 to 10000 LD50 units of botulinum neurotoxin per mL, more preferably from 10 to 2000 LD50 units of botulinum neurotoxin per mL, for example 20, 30, 40, 50, 75, 100, 200, 300, 400, 500, 600, 700, 800, 900, 1000 or 1500 LD50 units of botulinum neurotoxin per mL.

The quantity of botulinum neurotoxin can also be expressed in ng. The composition according to the invention preferably comprises from about 0.01 to 75 ng of botulinum neurotoxin per mL, more preferably from about 0.03 to 20 ng botulinum neurotoxin per mL, more preferably still from about 0.1 to 15 ng botulinum neurotoxin per mL, for example about 0.15, 0.3, 0.5, 0.75, 1, 2, 3, 4, 5, 6, 7, 8, 9 or 10 ng botulinum neurotoxin per mL.

The formulation according to the invention is animal protein free. In particular, the compositions according to the invention comprise no albumin, and in particular no human serum albumin. Preferably, the composition according to the invention is animal product free, meaning that they comprise no constituent of animal (including human) origin. Preferably, the composition according to the invention comprises no protein other than the proteinaceous neurotoxin. According to another embodiment, the composition according to the invention comprises no protein other than the proteinaceous neurotoxin and one or more NAPs (neurotoxin-associated proteins). For the sake of doubt, it is noted amino acids are not proteins.

According to an embodiment of the invention, the composition comprises no saccharides, including no monosaccharides, no disaccharides and no polysaccharides.

The liquid composition according to the invention is stable over time. For example, it is stable for 2 months at 2 to 8° C. According to one embodiment, it is stable for 3 months at 2 to 8° C., for example at 5° C. According to a preferred embodiment, it is stable for 6 months at 2 to 8° C., for example at 5° C. According to one embodiment, it is stable for 12 months at 2 to 8° C., for example at 5° C. According to one embodiment, it is stable for 18 months at 2 to 8° C., for example at 5° C. According to one embodiment, it is stable for 24 months at 2 to 8° C., for example at 5° C. According to one embodiment, it is stable for 36 months at 2 to 8° C., for example at 5° C. According to one embodiment, it is stable for 3 months at room temperature, for example at 25° C. According to one embodiment, it is stable for 6 months at room temperature, for example at 25° C. According to one embodiment, it is stable for 2 months at 37° C.

The liquid composition according to the invention is preferably stored at a temperature between 0° and 30° C. In a preferred embodiment it is stored at 2-8° C., for example at 5° C. In another embodiment, it is stored at room temperature. Preferably it is not frozen.

Stability can be assessed through comparison of the activity of the botulinum neurotoxin over time. Activity of the botulinum neurotoxin may refer to the ability of the activity of the botulinum neurotoxin to bind to its target receptor on a cell, to translocate the light chain into a cell, and/or to cleave its target SNARE protein.

Methods for measuring Botulinum neurotoxin activity are well known in the art. Botulinum neurotoxin activity can be assessed for example by using a mouse lethality assay (LD50) as described above, a muscle tissue based assay such as the mouse phrenic nerve hemidiaphragm assay (for example as described in Bigalke, H. and Rummel A., Toxins 7.12 (2015):4895-4905), a cell based assay (for example as described in WO201349508 or in WO2012166943) or an extracellular proteolytic activity assay such as BoTest® (Botulinum Neurotoxin Detection Kit available from Bio-Sentinel Inc.).

Preferably, a composition according to the invention is considered stable if there is no more than a given percentage of loss of activity over a given period of time and at a given temperature.

According to one embodiment, a composition according to the invention is considered stable if there is no more than 30% loss in extracellular proteolytic activity over 3, 6, 12, 18, 24 or 36 months at 2 to 8° C., for example no more than 30% loss in extracellular proteolytic activity over 6 months at 5° C. Preferably, a composition according to the invention is considered stable if there is no more than 20% loss in extracellular proteolytic activity over 3 months at 5° C., more preferably over 6, 12, 18, 24 or 36 months at 5° C. According to another embodiment, a composition according to the invention is considered stable if there is no more than 40% loss in extracellular proteolytic activity over 3 months at room temperature, for example at 25° C. Preferably, a composition according to the invention is considered stable if there is no more than 30% loss in extracellular proteolytic activity over 3 months at 25° C., more preferably over 6 months at 25° C. According to another embodiment, a composition according to the invention is considered stable if there is no more than 50% loss in extracellular proteolytic activity over 2 months at 37° C. Extracellular proteolytic activity can be measured with the BoTest® assay.

According to one embodiment, a composition according to the invention is considered stable if there is no more than 30% loss in MLD50 units over 2, 3, 6, 12, 18, 24 or 36 months at 2 to 8° C., for example no more than 30% loss in MLD50 units over 6 months at 5° C. Preferably, a composition according to the invention is considered stable if there is no more than 20% loss in MLD50 units over 2 months at 5° C., more preferably over 3, 6, 12, 18, 24 or 36 months at 5° C. According to another embodiment, a composition according to the invention is considered stable if there is no more than 40% loss in MLD50 units over 2 or 3 months at room temperature, for example at 25° C. Preferably, a composition according to the invention is considered stable if there is no more than 30% loss in MLD50 units over 3 months at 25° C., more preferably over 6 months at 25° C. According to another embodiment, a composition according to the invention is considered stable if there is no more than 50% loss in MLD50 units over 2 months at 37° C. MLD50 units can be measured as indicated above.

The liquid compositions according to the invention can be stored in sealed vials or syringes, for example glass vials or syringes, preferably type 1 (or "body neutral") glass vials or syringes. Preferably there is no or very little oxygen in the vial or syringe. The vials or syringes can for example be filled in an atmosphere with an oxygen below 100 ppm, preferably below 50 ppm, and nitrogen gas can be used as a protective atmosphere in the vials. When glass vials are used, they can for example be capped with chlorobutyl or bromobutyl rubber stoppers, which can be FluroTec® coated stoppers. Preferably, the liquid compositions according to the invention are stored in glass vials capped with Fluro-Tec® coated stoppers.

According to one embodiment, a liquid composition according to the invention comprises or consists essentially of:
 4 to 10000 LD50 units of botulinum neurotoxin per mL,
 0.001 to 15% v/v polysorbate,
 0.1 to 5 mg/mL tryptophan,
 10 to 500 mM NaCl,
 1 to 50 mM KCl,
 1 to 100 mM Sodium phosphate,
has a pH between 5.5 and 8, and is stable for 6 months at 5° C.

According to one embodiment, a liquid composition according to the invention comprises or consists essentially of:
 10 to 2000 LD50 units of botulinum neurotoxin per mL,
 0.005 to 2% v/v polysorbate,
 0.1 to 5 mg/mL tryptophan,
 25 to 300 mM NaCl,
 1 to 10 mM KCl,
 2 to 50 mM Sodium phosphate,
has a pH between 6.0 and 7.5, and is stable for 12 months at 5° C.

According to one embodiment, a liquid composition according to the invention comprises or consists essentially of:
 10 to 2000 LD50 units of botulinum neurotoxin per mL,
 0.05 to 0.2% v/v polysorbate 80,
 0.1 to 5 mg/mL tryptophan,
 25 to 300 mM NaCl,
 1 to 10 mM KCl,
 2 to 50 mM Sodium phosphate,
has a pH between 6.0 and 7.5, and is stable for 12 months at 5° C.

According to one embodiment, a liquid composition according to the invention comprises or consists essentially of:
 Botulinum neurotoxin A,
 0.2% v/v polysorbate 80,
 1 mg/mL tryptophan
 140 mM NaCl,
 3 mM KCl,
 10 mM Sodium phosphate,
wherein the pH of said composition is approximately 6.6.

According to another embodiment, a liquid composition according to the invention comprises or consists essentially of:
 Botulinum neurotoxin A,
 0.04% v/v polysorbate 80,
 1 mg/mL tryptophan
 140 mM NaCl,
 3 mM KCl,
 10 mM Sodium phosphate,
wherein the pH of said composition is approximately 6.9.

According to another embodiment, a liquid composition according to the invention comprises or consists essentially of:
 Botulinum neurotoxin B,
 0.25% v/v polysorbate 20,
 4 mg/mL tryptophan
 140 mM NaCl,
 3 mM KCl,
 10 mM Sodium phosphate,
wherein the pH of said composition is approximately 7.4.

According to another embodiment, a liquid composition according to the invention comprises or consists essentially of:
 Botulinum neurotoxin A,
 0.01% v/v polysorbate 80,
 0.25 mg/mL tryptophan
 255 mM NaCl,
 2 mM Sodium phosphate,
wherein the pH of said composition is approximately 7.2.

According to another embodiment, a liquid composition according to the invention comprises or consists essentially of:
 Botulinum neurotoxin A,
 0.01% v/v polysorbate 80,
 0.25 mg/mL tryptophan
 255 mM NaCl,
 10 mM KCl,
 50 mM Sodium phosphate,
wherein the pH of said composition is approximately 6.3.

According to another embodiment, a liquid composition according to the invention comprises or consists essentially of:
 Botulinum neurotoxin A,
 1% v/v polysorbate 80,
 0.25 mg/mL tryptophan
 255 mM NaCl,
 50 mM Sodium phosphate,
wherein the pH of said composition is approximately 6.3.

According to another embodiment, a liquid composition according to the invention comprises or consists essentially of:
 Botulinum neurotoxin A,
 1% v/v polysorbate 80,
 3 mg/mL tryptophan
 255 mM NaCl,
 10 mL KCl,
 50 mM Sodium phosphate,
wherein the pH of said composition is approximately 7.2.

According to another embodiment, a liquid composition according to the invention comprises or consists essentially of:
 Botulinum neurotoxin A,
 0.1% v/v polysorbate 80,
 1.625 mg/mL tryptophan
 140 mM NaCl,
 3 mM KCl,
 10 mM Sodium phosphate,
wherein the pH of said composition is approximately 6.75.

According to another embodiment, a liquid composition according to the invention comprises or consists essentially of:
Botulinum neurotoxin A,
0.01% v/v polysorbate 80,
1 mg/mL tryptophan
140 mM NaCl,
3 mM KCl,
10 mM Sodium phosphate,
wherein the pH of said composition is approximately 6.75.

According to another embodiment, a liquid composition according to the invention comprises or consists essentially of:
Botulinum neurotoxin A,
0.1% v/v polysorbate 80,
1 mg/mL tryptophan
140 mM NaCl,
3 mM KCl,
10 mM Sodium phosphate,
wherein the pH of said composition is approximately 6.75.

According to another embodiment, a liquid composition according to the invention comprises or consists essentially of:
Botulinum neurotoxin A,
1% v/v polysorbate 80,
1 mg/mL tryptophan
140 mM NaCl,
3 mM KCl,
10 mM Sodium phosphate,
wherein the pH of said composition is approximately 6.75.

According to another embodiment, a liquid composition according to the invention comprises or consists essentially of:
Botulinum neurotoxin B,
15% v/v polysorbate 20,
1 mg/mL tryptophan
140 mM NaCl,
3 mM KCl,
10 mM Sodium phosphate,
wherein the pH of said composition is approximately 7.4.

According to another embodiment, a liquid composition according to the invention comprises or consists essentially of:
Botulinum neurotoxin B,
15% v/v polysorbate 20,
4 mg/mL tryptophan
140 mM NaCl,
3 mM KCl,
10 mM Sodium phosphate,
wherein the pH of said composition is approximately 7.4.

According to another embodiment, a liquid composition according to the invention comprises or consists essentially of:
Botulinum neurotoxin B,
0.25% v/v polysorbate 20,
4 mg/mL tryptophan
140 mM NaCl,
3 mM KCl,
10 mM Sodium phosphate,
wherein the pH of said composition is approximately 7.4.

Another aspect is the use of the liquid compositions according to the invention in therapy.

The liquid compositions according to the invention can be used in therapy to treat or prevent muscular disorders, neuromuscular disorders, neurological disorders, ophtalmological disorders, pain disorders, psychological disorders, articular disorders, inflammatory disorders, endocrine disorders or urological disorders.

For example, the liquid compositions according to the invention can be used for treating or preventing a disease, condition or syndrome selected from the following:

ophtalmological disorders selected from the group consisting of blepharospasm, strabismus (including restrictive or myogenic strabismus), amblyopia, oscillopsia, protective ptosis, therapeutic ptosis for corneal protection, nystagmus, estropia, diplopia, entropion, eyelid retraction, orbital myopathy, heterophoria, concomitant misalignment, nonconcomitant misalignment, primary or secondary esotropia or exotropia, internuclear ophthalmoplegia, skew deviation, Duane's syndrome and upper eyelid retraction;

movement disorders including hemifacial spasm, torticollis, spasticity of the child or of the adult (e.g. in cerebral palsy, post-stroke, multiple sclerosis, traumatic brain injury or spinal cord injury patients), idiopathic focal dystonias, muscle stiffness, Writer's cramp, hand dystonia, VI nerve palsy, oromandibular dystonia, head tremor, tardive dyskinesia, tardive dystonia, occupational cramps (including musicians' cramp), facial nerve palsy, jaw closing spasm, facial spasm, synkinesia, tremor, primary writing tremor, myoclonus, stiff-person-syndrome, foot dystonia, facial paralysis, painful-arm-and-moving-fingers-syndrome, tic disorders, dystonic tics, Tourette's syndrome, neuromyotonia, trembling chin, lateral rectus palsy, dystonic foot inversion, jaw dystonia, Rabbit syndrome, cerebellar tremor, III nerve palsy, palatal myoclonus, akasthesia, muscle cramps, IV nerve palsy, freezing-of-gait, extensor truncal dystonia, post-facial nerve palsy synkinesis, secondary dystonia, Parkinson's disease, Huntington's chorea, epilepsy, off period dystonia, cephalic tetanus, myokymia and benign cramp-fasciculation syndrome;

otorhinolaryngological disorders including spasmodic dysphonia, otic disorders, hearing impairment, ear click, tinnitus, vertigo, Meniere's disease, cochlear nerve dysfunction, stuttering, cricopharyngeal dysphagia, bruxism, closure of larynx in chronic aspiration, vocal fold granuloma, ventricular dystonia, ventricular dysphonia, mutational dysphonia, trismus, snoring, voice tremor, aspiration, tongue protrusion dystonia, palatal tremor, deep bite of lip and laryngeal dystonia; First Bite Syndrome;

gastrointestinal disorders including achalasia, anal fissure, constipation, temperomandibular joint dysfunction, sphincter of Oddi dysfunction, sustained sphincter of Oddi hypertension, intestinal muscle disorders, puborectalis syndrome, anismus, pyloric spasm, gall bladder dysfunction, gastrointestinal or oesophageal motility dysfunction, diffuse oesophageal spasm and gastroparesis;

urogenital disorders including detrusor sphincter dyssynergia, detrusor hyperreflexia, neurogenic bladder dysfunction (e.g. in Parkinson's disease, spinal cord injury, stroke or multiple sclerosis patients), overactive bladder, neurogenic detrusor overactivity, bladder spasms, urinary incontinence, urinary retention, hypertrophied bladder neck, voiding dysfunction, interstitial cystitis, vaginismus, endometriosis, pelvic pain, prostate gland enlargement (Benign Prostatic Hyperplasia), prostatodynia, prostate cancer and priapism;

dermatological disorders including cutaneous cell proliferative disorders, skin wounds, psoriasis, rosacea, acne;

rare hereditary skin disorders such as Fox-Fordyce syndrome or Hailey-Hailey disease; keloid and hypertrophic scar reduction; pore size reduction; inflammatory conditions of the skin; painful inflammatory conditions of the skin;

pain disorders including back pain (upper back pain, lower back pain), myofascial pain, tension headache, fibromyalgia, painful syndromes, myalgia, migraine, whiplash, joint pain, post-operative pain, pain not associated with a muscle spasm and pain associated with smooth muscle disorders;

inflammatory disorders including pancreatitis, neurogenic inflammatory disorders (including gout, tendonitis, bursitis, dermatomyositis and ankylosing spondylitis);

secretory disorders such as excessive gland secretions, hyperhidrosis (including axillary hyperhidrosis, palmar hyperhidrosis and Frey's syndrome), hypersalivation, sialorrhoea, bromhidrosis, mucus hypersecretion, hyperlacrimation, holocrine gland dysfunction; excess sebum secretion;

respiratory disorders including rhinitis (including allergic rhinitis), COPD, asthma and tuberculosis;

hypertrophic disorders including muscle enlargement, masseteric hypertrophy, acromegaly and neurogenic tibialis anterior hypertrophy with myalgia;

articular disorders including tennis elbow (or epicondylitis of the elbow), inflammation of joints, coxarthrosis, osteoarthritis, rotator muscle cap pathology of the shoulder, rheumatoid arthritis and carpal tunnel syndrome;

endocrine disorders like type 2 diabetes, hyperglucagonism, hyperinsulinism, hypoinsulinism, hypercalcemia, hypocalcemia, thyroid disorders (including Grave's disease, thyroiditis, Hashimoto's thyroiditis, hyperthyroidism and hypothyroidism), parathyroid disorders (including hyperparathyroidism and hypoparathyroidism), Gushing's syndrome and obesity;

autoimmune diseases like systemic lupus erythemotosus;

proliferative diseases including paraganglioma tumors, prostate cancer and bone tumors;

traumatic injuries including sports injuries, muscle injuries, tendon wounds and bone fractures; and veterinary uses (e.g. immobilisation of mammals, equine colic, animal achalasia or animal muscle spasms).

The liquid compositions according to the invention can also be used in aesthetic medicine (that is for improving cosmetic appearance), in particular for treating or preventing skin wrinkles, in particular facial wrinkles such as facial frown lines, wrinkles of the contour of the eye, glabellar frown lines, downturned mouth, wrinkles of the neck (platysmal bands), wrinkles of the chin (mentalis, peau d'orange, dimpled chin), forehead lines, "scratched skin" wrinkles, nasal lift treatment or sleep lines. According to this aspect of the invention, the subject to be treated or prevented for improving cosmetic appearance is preferably not suffering from any of the disorders, conditions or syndromes that are described above. More preferably, said subject is a healthy subject (i.e. not suffering from any disease, condition or syndrome).

The liquid compositions according to the invention can be used in combination with another therapeutic compound. In one embodiment the liquid compositions according to the invention is administered in combination with an analgesic compound for treating pain, in particular in combination with an opioid derivative such as morphine as described in WO 2007/144493 the content of which is herein incorporated by reference. In another embodiment, the liquid compositions according to the invention is administered in combination with hyaluronic acid, for example for treating prostate cancer as described in WO 2015/044416 the content of which is herein incorporated by reference.

A further aspect of the present invention is the use of an amino acid selected from tryptophan and tyrosine to protect a proteinaceous neurotoxin from degradation in a liquid composition which is free of animal derived proteins.

According to a preferred embodiment, the amino acid is tryptophan, more preferably L-tryptophan.

Preferably, the proteinaceous neurotoxin is a botulinum neurotoxin. According to an embodiment of the invention, the botulinum neurotoxin is a botulinum neurotoxin in complex form. According to another embodiment, the botulinum neurotoxin is a high purity botulinum neurotoxin. According to an embodiment of the invention, the botulinum neurotoxin is a botulinum neurotoxin purified from its natural clostridial strain. According to another embodiment, botulinum neurotoxin is a botulinum neurotoxin produced recombinantly in a heterologous host such as E. coli. According to the present invention, the Botulinum neurotoxin can be a BoNT of serotype A, B, C, D, E, F or G. According to the present invention, a botulinum neurotoxin can be a modified botulinum neurotoxin as described above. According to the present invention, a recombinant botulinum neurotoxin can be a chimeric botulinum neurotoxin as described above.

According to a preferred embodiment, the amino acid is used in combination with a surfactant and a buffer comprising sodium, chloride and phosphate ions, and the liquid composition has a pH between 5.5 and 8. Preferably, the surfactant is a non-ionic surfactant, more preferably a polysorbate, for example PS20, PS60 or PS80. Most preferably, the non-ionic surfactant is PS80. Preferably, the buffer also comprises potassium ions. The buffer can for example be obtained by combining sodium chloride, potassium chloride and sodium phosphate salts. According to a preferred embodiment, the pH is between 6.0 and 7.5, for example 6.3, 6.35, 6.4, 6.45, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5. Preferably the pH is within one unit from physiological pH (which is around 7.4).

According to a preferred embodiment of the use according to the invention, the liquid composition is stable for 2 months. For example, it is stable for 2 months at 2 to 8° C. According to one embodiment, it is stable for 3 months at 2 to 8° C., for example at 5° C.

According to a preferred embodiment, it is stable for 6 months at 2 to 8° C., for example at 5° C. According to one embodiment, it is stable for 12 months at 2 to 8° C., for example at 5° C. According to one embodiment, it is stable for 18 months at 2 to 8° C., for example at 5° C. According to one embodiment, it is stable for 24 months at 2 to 8° C., for example at 5° C. According to one embodiment, it is stable for 36 months at 2 to 8° C., for example at 5° C. According to one embodiment, it is stable for 3 months at room temperature, for example at 25° C. According to one embodiment, it is stable for 6 months at room temperature, for example at 25° C.

EXAMPLES

1. Preparation of Stable Liquid Botulinum Toxin A Formulations

Liquid botulinum toxin preparations containing 15 ng/mL of highly purified BoNT/A, 15% v/v polysorbate 20, an amino acid selected from tyrosine (Tyr), tryptophan (Trp) and cysteine (Cys) or a mixture of methionine (Met), tyrosine (Tyr), tryptophan (Trp) and cysteine (Cys) (Sigma Aldrich), and Phosphate Buffer Saline (PBS from Calbiochem) (140 mM NaCl, 10 mM sodium phosphate and 3 mM KCl at pH 7.4 at 25° C.) were prepared, filtered using 0.22 µm PVDF (polyvinylidenflourid) filters and stored in siliconized 2 mL glass syringes for 6 days at 40° C., after which a potency test was performed for each preparation.

For the potency test, the syringes containing the preparations were emptied in 2 mL glass vials (Chromacol, Gold) with lids containing PTFE treated rubber septa (Chromacol) or in 1.7 mL plastic micro centrifuge tubes (Axygen, Maximum Recovery) which both have low protein adsorption properties. The preparations were subsequently diluted using 0.9% NaCl solution with 3% human serum albumin (HSA). For each preparation, 50 μL of sample was injected into the Gastrocnemius muscle of mice on the same day as the dilution was performed. The mice were monitored for 3 days and the degree of paralysis was recorded.

The results are shown in table 1.

TABLE 1 an accelerated storage test (6 days at 40° C.) of amino acid additions on BoNT/A stability.

| Formulation | | | Potency test | | | | |
|---|---|---|---|---|---|---|---|
| | BoNT/A | | Dilution in 0.9 NaCl with 3% | Inj. Dose | Potency rating | | |
| Buffer | conc. | Amino acid | HSA (times) | (ng) | Day 1 | Day 2 | Day 3 |
| PBS pH 7.4 15% polysorbate 20 | 15 ng/mL | Trp 0.25 mg/mL + Cys 0.25 mg/mL + Met 0.25 mg/mL + Tyr 0.25 mg/mL | 2× 20× | 0.25 0.025 | — — | — — | WN WN |
| | | Cys 1 mg/mL | 2× 20× | 0.25 0.025 | — — | — — | WN WN |
| | | Tyr 0.74 mg/mL | 2× | 0.25 | — | — | Sharp PA whole abdomen |
| | | | 20× | 0.025 | — | — | WN |
| | | Trp 1 mg/mL | 2× 20× | 0.25 0.025 | — — | † — | WN |
| | | — | 2× 20× | 0.25 0.025 | — — | — — | WN WN |

Paralysis results in mice: — = not analysed, WN = without note, PA = paralysis and † = death.

Tyrosine and tryptophan were found to have a protective effect against BoNT/A degradation. Tryptophan was found to have the strongest protective effect. Cysteine, as well as the mixture containing all 4 amino acids did not have a protective effect.

2. Preparation of a Stable Liquid Botulinum Toxin B Formulation

Liquid botulinum toxin preparations containing 350 ng/mL of highly purified BoNT/B, 15% v/v polysorbate 20, an amino acid selected from tyrosine (Tyr), tryptophan (Trp) and cysteine (Cys) or a mixture of methionine (Met), tyrosine (Tyr), tryptophan (Trp) and cysteine (Cys), and Phosphate Buffer Saline (PBS) at pH 7.4 were prepared, filtered using 0.22 μm filters and stored in siliconized 2 mL glass syringes for two weeks at 40° C., after which a potency test was performed for each preparation as described above.

The results are shown in table 2.

TABLE 2 an accelerated storage test (two weeks at 40° C.) of amino acid additions on BoNT/B stability.

| Formulation | | | Potency test | | | | |
|---|---|---|---|---|---|---|---|
| | BoNT/B | | Dilution in 0.9 NaCl with 3% | Inj. Dose | Potency rating | | |
| Buffer | conc. | Amino acid | HSA (times) | (ng) | Day 1 | Day 2 | Day 3 |
| PBS pH 7.4 15% polysorbate 20 | 350 ng/mL | Trp 0.25 mg/mL + Cys 0.25 mg/mL + Met 0.25 mg/mL + Tyr 0.25 mg/mL | 10× | 1.75 | — | — | PA |
| | | Cys 1 mg/mL | 10× | 1.75 | — | — | PA |
| | | Tyr 0.575 mg/mL | 10× | 1.75 | — | † | |
| | | Trp 1 mg/mL | 10× | 1.75 | — | † | |
| | | | 35× | 0.5 | — | — | PA |

Paralysis results in mice: — = not analysed, WN = without note, PA = paralysis and † = death.

Tyrosine and tryptophan were found to have a protective effect against BoNT/B degradation. Cysteine, as well as the mixture containing all 4 amino acids also had a protective effect but to a weaker extent.

3. Evaluation of Different Concentrations of Tryptophan and Polysorbate 20

Liquid botulinum toxin preparations containing highly purified BoNT/A or BoNT/B and various concentrations of polysorbate 20 (PS 20) and tryptophan and Phosphate Buffer Saline (PBS) at pH 7.4 were prepared, filtered using 0.22 μm filters and stored in siliconized 2 mL glass syringes. Hind limb paralysis potency tests were performed for each preparation as described above.

The results are shown in table 3.

TABLE 3 evaluation of Trp and polysorbate 20 (PS20) concentrations on BoNT/A or BoNT/B stability.

| | Formulation | | | | | POTENCY TESTING | | | | | | | | |
|---|---|---|---|---|---|---|---|---|---|---|---|---|---|---|
| | | | | | | Potency rating (1-3 d) for samples stored at different temperatures and lengths | | | | | | | | |
| | BoNT | | | Dilution in 0.9 | Inj. | 5° C. | | | 25° C. | | | | | |
| | conc. | Trp | PS20 | NaCl with 3% | Dose | 6 months | | | 5 weeks | | | 4 months | | |
| BoNT | (ng/mL) | (mg/mL) | (%) | HSA (times) | (ng) | 1 d | 2 d | 3 d | 1 d | 2 d | 3 d | 1 d | 2 d | 3 d |
| BoNT/A | 15 | 8 | 15 | 1× | 0.75 | — | † | | — | — | † | — | — | PA |
| | | | | 5× | 0.15 | — | — | † | — | — | † | — | — | WN |
| | 15 | 8 | 0.25 | 1× | 0.75 | — | † | | — | — | †* | — | — | † |
| | | | | 5× | 0.15 | — | — | † | — | †* | | — | — | WN² |
| | 15 | 1 | 15 | 1× | 0.75 | — | † | | — | † | | † | | |
| | | | | 5× | 0.15 | — | — | † | — | — | † | — | † | PA³ |
| BoNT/B | 100 | 8 | 15 | 1× | 5 | — | — | † | — | — | † | — | — | PA |
| | | | | 10× | 0.5 | — | — | PA¹ | — | — | PA | — | — | PA |
| | 100 | 8 | 0.25 | 1× | 5 | — | — | † | — | — | † | † | | |
| | | | | 10× | 0.5 | — | — | PA⁴ | — | — | WN¹ | — | — | PA |
| | 100 | 1 | 15 | 1× | 5 | — | — | † | — | — | † | † | | |
| | | | | 10× | 0.5 | — | — | PA⁴ | — | — | PA | — | — | PA |

Paralysis results in mice: — = not analysed, WN = without note, PA = paralysis and † = death.
Paralysis degree (PA):
¹Toes affected;
²Slightly numb in hind leg;
³Both hind legs paralysed;
⁴Hind leg paralysed; Elution buffer from purification (5): 50 mM sodium acetate pH 4.5 with 0.2% (v:v) polysorbate 20 and 400 mM sodium chloride.
*a mix up of two BoNT/A dilutions of the 25° C. 8 mg/mL Trp 0.25% polysorbate 20 has probably occurred.

4. Evaluation of Different Salt Concentrations in BoNT/B Preparations

Liquid botulinum toxin preparations containing 100 ng/mL of highly purified BoNT/B, polysorbate 20, tryptophan from various amino acid suppliers and a buffer selected from PBS pH 7.4 (Calbiochem), 12 nM phosphate buffer pH 7 (Apoteket) and 20 mM sodium acetate (NaAc) pH 5.5 (NaAc from Fluka and acetic acid from Merck) were prepared, filtered using 0.22 μm filters and stored in siliconized 2 mL glass syringes. Hind limb paralysis potency tests were performed for each preparation as described above.

The results are shown in table 4.

TABLE 4 evaluation of different salt concentrations on stability of BoNT/B.

| | | | | | | Potency testing | | | Potency rating (1-3 d) for samples stored at different length | | |
|---|---|---|---|---|---|---|---|---|---|---|---|
| BoNT/B | | Trp | | Dilution in 0.9 | Inj. | | | | 40° C. | | |
| conc. | | manufacturer | PS20 | NaCl with 3% | Dose | 2 weeks | | | 5 weeks | | |
| (ng/mL) | Buffer | and conc. | (%) | HSA (times) | (ng) | 1 d | 2 d | 3 d | 1 d | 2 d | 3 d |
| 100 | PBS pH 7.4 | Ajinomoto 4 mg/mL | 15 | 1× | 5 | — | † | | | | |
| | | | | 10× | 0.5 | — | — | PA | | | |
| 100 | PBS pH 7.4 | Sigma Aldrich 4 mg/mL | 15 | 1× | 5 | — | † | | | | |
| | | | | 10× | 0.5 | — | — | PA | | | |
| 100 | PBS pH 7.4 | Sigma Aldrich 1 mg/mL | 15 | 1× | 5 | — | † | | | | |
| | | | | 10× | 0.5 | — | — | PA | | | |
| 100 | PBS pH 7.4 | Sigma Aldrich 4 mg/mL | 0.25 | 1× | 5 | — | † | | — | † | |
| | | | | 10× | 0.5 | — | — | PA | — | — | PA² |

TABLE 4-continued evaluation of different salt concentrations on stability of BoNT/B.

| BoNT/B conc. (ng/mL) | Buffer | Trp manufacturer and conc. | PS20 (%) | Dilution in 0.9 NaCl with 3% HSA (times) | Inj. Dose (ng) | Potency rating (1-3 d) for samples stored at different length 40° C. | | | | | |
|---|---|---|---|---|---|---|---|---|---|---|---|
| | | | | | | 2 weeks | | | 5 weeks | | |
| | | | | | | 1 d | 2 d | 3 d | 1 d | 2 d | 3 d |
| 100 | 12 mM Phosphate pH 7 | Sigma Aldrich 4 mg/mL | 15 | 1× 10× | 5 0.5 | — — | — — | WN WN[1] | | | |
| 100 | 20 mM NaAc pH 5.5 | Sigma Aldrich 4 mg/mL | 15 | 1× 10× | 5 0.5 | — — | — — | PA PA | | | |

Paralysis results in mice: — = not analysed, WN = without note, PA = paralysis and † = death.
[1]Some loss of function;
[2]Weak paralysis The results show that the preparations containing the PBS buffer (containing sodium, chloride, phosphate and potassium ions) appears to play a role in the stability of the botulinum toxin.

5. Evaluation of Different Stabilizers

Liquid botulinum toxin preparations containing 15 ng/mL of highly purified BoNT/A, a polysorbate 20 (PS20) or polysorbate 80 (PS80) or HSA, tryptophan and PBS were prepared, filtered using 0.22 μm filters and stored in siliconized 2 mL glass syringes. Hind limb paralysis potency tests were performed for each preparation as described above.

The results are shown in table 5.

7. Evaluation of Different Formulations

Liquid botulinum toxin preparations containing 0.3 ng/mL of highly purified BoNT/A, a polysorbate selected from PS20 and PS80, 1 mg/mL tryptophan and 12 mM PBS at pH 7.4 were prepared as described above. The pH of each preparation was adjusted to pH 6.6 or 6.9 by adding 1.2 M HCl.

Polysorbate 20 was tested at one concentration, 0.2% w/v, corresponding to about 20 times its CMC (critical micellar concentration, about 0.01% w/v at 21° C.). Polysorbate 80 was tested 0.04% and 0.2% w/v, corresponding respectively to about 20 and 100 times its CMC (about 0.002% w/v at 21° C.).

TABLE 5 evaluation of different surfactants on stability of BoNT/A.

| BoNT/A conc. (ng/ml) | Buffer | Trp | Stabiliser | Dilution in 0.9 NaCl with 3% HSA (times) | Inj. Dose (ng) | Potency rating (1-3 d) for samples stored at different length 40° C. | | | | | | | | |
|---|---|---|---|---|---|---|---|---|---|---|---|---|---|---|
| | | | | | | 6 days | | | 4 weeks | | | 3 months | | |
| | | | | | | 1 d | 2 d | 3 d | 1 d | 2 d | 3 d | 1 d | 2 d | 3 d |
| 15 | PBS pH 7.4 | 1 mg/mL | PS 80 0.25% | 1.7× 15× | 0.45 0.05 | † † | | | † † | | | — — | — — | PA[3] WA |
| 15 | PBS pH 7.4 | 1 mg/mL | PS 20 0.25% | 1.7× 15× | 0.45 0.05 | † † | | | † — | — | PA | — — | — — | PA[2] WN |
| 15 | PBS pH 7.4 | — | HSA 1 mg/mL | 1.7× 15× | 0.45 0.05 | † † | | | † † | | | — — | † — | PA[1] |

Paralysis results in mice: — = not analysed, WN = without note, PA = paralysis and † = death.
[1]Severe paralysis both hind legs;
[2]Angles paws;
[3]Severe paralysis 6. Evaluation of Different Formulations Liquid botulinum toxin preparations containing 10 ng/mL of highly purified BoNT/A, 0.25% PS80, 1 mg/mL tryptophan and PBS were prepared as described above. The pH was adjusted to 6.6 and 7.0 by adding HCl. Each preparation was stored 5 weeks at 40° C.

Each preparation was then diluted 10 times and hind limb paralysis potency tests were performed as described above (0.05 ng per injection). In both cases, hind limb paralysis was observed at day 3. The paralysis was stronger with the pH 6.6 preparation.

TABLE 6

Choice of polysorbate and pH

| Composition | PS20% w/v | PS20% w/v | pH |
|---|---|---|---|
| PS20-1 | 0.2 | — | 6.6 |
| PS20-2 | 0.2 | — | 6.9 |
| PS80-1 | — | 0.04 | 6.6 |
| PS80-2 | — | 0.04 | 6.9 |
| PS80-3 | — | 0.2 | 6.6 |

For each preparation, a volume of 0.5 mL was filled in 1 mL long glass syringes (BD) and sealed with a fluorocarbon coated plunger.

The potency was measured by hind limb paralysis test on mice as described above.

No decrease in potency was observed in any formulation after 6 months storage at 5° C. and after 25° C.

8. Evaluation of Different Formulations

Nineteen different formulations containing highly purified botulinum neurotoxin type A were prepared with varying concentrations of polysorbate 80, tryptophan, sodium phosphate, sodium chloride, potassium chloride and varying pH. Each formulation had a target nominal potency of 500 U/mL. Each formulation was degassed, filtered through 0.2 µm filter and filled into vials. Nitrogen gas was used as a protective atmosphere in the vials. The filling was performed in an anaerobic chamber. Each formulation was filled in 1 mL aliquots in a nitrogen atmosphere in 2 mL glass vials capped with FluroTec® stoppers sealed with aluminium flip off seals and stored upright.

The stability of the 19 formulations was assessed at 5° C., 25° C. and 37° C. using BoTest® to measure potency.

TABLE 7

Excipient compositions

| Exp Name | pH | Sodium phosphate (mM) | Tryptophan (mg/mL) | Poly-sorbate 80 (v %) | NaCl (mM) | KCl (mM) |
|---|---|---|---|---|---|---|
| N1 | 6.3 | 2 | 0.25 | 0.01 | 25 | 0 |
| N2 | 7.2 | 2 | 0.25 | 0.01 | 255 | 0 |
| N3 | 6.3 | 50 | 0.25 | 0.01 | 255 | 10 |
| N4 | 7.2 | 50 | 0.25 | 0.01 | 25 | 10 |
| N5 | 6.3 | 2 | 3 | 0.01 | 255 | 10 |
| N6 | 7.2 | 2 | 3 | 0.01 | 25 | 10 |
| N7 | 6.3 | 50 | 3 | 0.01 | 25 | 0 |
| N8 | 7.2 | 50 | 3 | 0.01 | 255 | 0 |
| N9 | 6.3 | 2 | 0.25 | 1 | 25 | 10 |
| N10 | 7.2 | 2 | 0.25 | 1 | 255 | 10 |
| N11 | 6.3 | 50 | 0.25 | 1 | 255 | 0 |
| N12 | 7.2 | 50 | 0.25 | 1 | 25 | 0 |
| N13 | 6.3 | 2 | 3 | 1 | 255 | 0 |
| N14 | 7.2 | 2 | 3 | 1 | 25 | 0 |
| N15 | 6.3 | 50 | 3 | 1 | 25 | 10 |
| N16 | 7.2 | 50 | 3 | 1 | 255 | 10 |
| N17 | 6.75 | 10 | 1.625 | 0.1 | 140 | 3 |

TABLE 8

Packaging components

| Article | Article number, Supplier |
|---|---|
| Clear glass vial of boro silicate Type I plus, 2 mL | 1097221, Schott |
| Grey Flurotec coated bromobutyl stopper Westar RS, 13 mm | 1356 4023/50, West |
| Aluminium flip off seals, 13 mm | 5920-6623, West |

For all formulations the solution remained clear and for most parts colourless.

The excipients concentrations tested in this study seem not to affect the pH of the formulations during the time interval tested. The potency results are presented in table 9.

TABLE 9

Botest potency results

| | | | Remaining potency compared to base line (BoTest) | | | | |
|---|---|---|---|---|---|---|---|
| | | Baseline potency (U/mL) (Botest) | 2 months 37° C. | | 6 months 25° C. | | 6 months 5° C. | |
| | pH | 0 month | U/mL | % | U/mL | % | U/mL | % |
| N1 | 6.3 | 86 | 0 | 0 | 0 | 0 | 39 | 45 |
| N2 | 7.2 | 474 | 210 | 44 | 389 | 82 | 485 | 102 |
| N3 | 6.3 | 449 | 288 | 64 | 406 | 90 | 512 | 114 |
| N4 | 7.2 | 299 | 62 | 21 | 368 | 123 | 406 | 136 |
| N5 | 6.3 | 378 | 263 | 70 | 385 | 102 | 422 | 112 |
| N6 | 7.2 | 93 | 0 | 0 | 0 | 0 | 52 | 56 |
| N7 | 6.3 | 238 | 0 | 0 | 0 | 0 | 239 | 100 |
| N8 | 7.2 | 375 | 305 | 81 | 402 | 107 | 450 | 120 |
| N9 | 6.3 | 196 | 0 | 0 | 100 | 51 | 294 | 150 |
| N10 | 7.2 | 354 | 201 | 57 | 408 | 115 | 411 | 116 |
| N11 | 6.3 | 438 | 197 | 45 | 372 | 85 | 492 | 112 |
| N12 | 7.2 | 411 | 96 | 23 | 295 | 72 | 417 | 101 |
| N13 | 6.3 | 304 | 185 | 61 | 403 | 133 | 416 | 137 |
| N14 | 7.2 | 206 | 0 | 0 | 0 | 0 | 183 | 89 |
| N15 | 6.3 | 197 | 155 | 79 | 231 | 117 | 214 | 109 |
| N16 | 7.2 | 476 | 227 | 48 | 390 | 82 | 685 | 144 |
| N17 | 6.75 | 402 | 250 | 62 | 286 | 71 | 488 | 121 |

For several compositions there was no more than 30% loss in potency over 6 months at 5° C. and/or no more than about 40% loss in potency over 3 months at 25° C. and/or no more than about 50% loss in potency over 2 months at 37° C.

9. Evaluation of PS 60

A formulation containing highly purified botulinum neurotoxin type A was prepared with 0.1% (v/v) PS60, 1 mg/mL L-Tryptophan, 10 mM sodium phosphate, 140 mM sodium chloride, 3 mM potassium chloride and water for injection. The pH was adjusted to 6.75 with HCl. The formulation had a target nominal potency of 100 U/mL. The formulation was degassed, filtered through 0.2 µm filters and filled into 2 mL vials aseptically in an anaerobic chamber with nitrogen atmosphere with a fill volume of 1 mL. Nitrogen gas was used as protective atmosphere in the vials. The vials were capped with FluroTec® stoppers sealed with aluminium flip off seals.

TABLE 10

Packaging components

| Article | Article number, Supplier |
|---|---|
| Clear glass vial of boro silicate Type I plus, 2 mL | 1097221, Schott |
| 13 mm Inj stopper coated bromobutyl 4023-50 grey | INJ13TB3WRS, Nordic Pack |
| Blue aluminium flip off seals, 13 mm | 5920-1164, Nordic Pack |

The potency over time at 37° C. and 25° C. was measured by the MLD50 test as described herein.

At 37° C., the remaining potency after 9 weeks was around 50-55% of the initial potency.

At 25° C., the remaining potency after 3 months was about 80% of the initial potency.

The invention claimed is:

1. A liquid composition comprising:
  (i) 4 to 10,000 units/ml of a botulinum neurotoxin;
  (ii) 0.01 to 1 vol % of a polysorbate;
  (iii) an amino acid selected from tryptophan and tyrosine; and
  (iv) a buffer comprising sodium, chloride, and phosphate ions,
  wherein:
  the liquid composition has a pH between 6.3 and 7.2 and is free of animal derived proteins;
  the amino acid is present at a concentration of from about 0.25 mg/ml to about 5 mg/ml and protects the botulinum neurotoxin from degradation, thereby providing a liquid composition that is stable for at least 2 months at 2 to 8° C.; and
  the composition does not comprise albumin, and
  the composition comprises phosphate ions at 50 mM or greater.

2. The liquid composition of claim 1, wherein the polysorbate is Polysorbate 20, Polysorbate 60 or Polysorbate 80.

3. The liquid composition of claim 1, wherein the amino acid is tryptophan.

4. The liquid composition of claim 1, wherein the buffer comprises potassium ions.

5. The liquid composition of claim 1, wherein no more than a 30% loss in extracellular proteolytic activity occurs over 2, 3, 6, 12, 18, 24 or 36 months at 5° C.

6. The liquid composition of claim 1, wherein the botulinum neurotoxin is a natural botulinum neurotoxin in complex form, a high purity natural botulinum neurotoxin, or a recombinant botulinum neurotoxin.

7. The liquid composition of claim 6, wherein the botulinum neurotoxin is a recombinant botulinum neurotoxin selected from a botulinum neurotoxin A, B, C, D, E, F or G, a modified botulinum neurotoxin, or a chimeric botulinum neurotoxin.

8. The liquid composition of claim 1, comprising:
  4 to 10000 LD50 units of the botulinum neurotoxin per mL;
  0.001 to 1% v/v of the polysorbate;
  0.575 mg/ml to 5 mg/ml tryptophan;
  10 to 500 mM NaCl;
  1 to 50 mM KCl; and
  50 to 100 mM sodium phosphate;
  wherein the composition is stable for 6 months at 5° C.

9. The liquid composition of claim 8, comprising:
  10 to 2000 LD50 units of botulinum neurotoxin per mL;
  0.05 to 0.2% v/v polysorbate 80;
  0.575 mg/ml to 5 mg/ml tryptophan;
  25 to 300 mM NaCl;

1 to 10 mM KCl; and
50 to 100 mM sodium phosphate;
wherein the composition has a pH between 6.3 and 7.2 and is stable for 12 months at 5° C.

10. The liquid composition of claim 1, wherein the amino acid is L-tryptophan.

11. The liquid composition of claim 1, wherein the amino acid is present at a concentration of about 0.575 mg/ml to about 3 mg/ml.

12. The liquid composition of claim 1, wherein the amino acid is present at a concentration of about 0.74 mg/ml to about 5 mg/ml.

13. The liquid composition of claim 1, wherein the amino acid is present at a concentration of about 0.74 mg/ml to about 3 mg/ml.

14. A stabilized, botulinum neurotoxin ready-to-use (RTU) liquid composition comprising:
   4 to 10000 LD50 units of botulinum neurotoxin per mL;
   0.001 to 1% v/v polysorbate;
   0.25 mg/mL to 5 mg/mL amino acid selected from tryptophan and tyrosine;
   10 to 500 mM NaCl;
   1 to 50 mM KCl; and
   50 to 100 mM sodium phosphate;
   wherein:
      the composition has a pH between 6.3 and 7.2;
      the composition does not comprise albumin; and
      the amino acid at a concentration of 0.25 to 5 mg/mL protects the botulinum neurotoxin from degradation, thereby providing a liquid composition that is stable for at least 2 months at 2 to 8° C. wherein no more than a 30% loss in extracellular proteolytic activity occurs over 2, 3, 6, 12, 18, 24 or 36 months at 5° C.

15. The stabilized, botulinum neurotoxin ready-to-use (RTU) liquid composition of claim 14, comprising:
   10 to 2000 LD50 units of the botulinum neurotoxin per mL;
   0.05 to 0.2% v/v polysorbate 80;
   0.575 mg/ml to 5 mg/ml tryptophan;
   25 to 300 mM NaCl;
   1 to 10 mM KCl; and
   2 to 50 mM sodium phosphate;
   wherein the composition is stable for 12 months at 5° C.

16. A liquid composition comprising:
   (i) 4 to 10,000 units/ml of a botulinum neurotoxin;
   (ii) 0.01 to 1 vol % of a polysorbate;
   (iii) an amino acid selected from tryptophan and tyrosine; and
   (iv) a buffer comprising sodium, chloride, and phosphate ions,
   wherein:
      the liquid composition has a pH between 6.3 and 7.2 and is free of animal derived proteins;
      the amino acid is present at a concentration of from about 0.25 mg/ml to about 5 mg/ml and protects the botulinum neurotoxin from degradation, thereby providing a liquid composition that is stable for at least 2 months at 2 to 8° C.;
      the composition does not comprise albumin;
      the composition comprises less than 50 mM phosphate ions; and
      the composition comprises sodium ions at 150 mM or greater or the polysorbate at 1 vol %.

* * * * *